US010481090B2

(12) United States Patent
Falk et al.

(10) Patent No.: US 10,481,090 B2
(45) Date of Patent: Nov. 19, 2019

(54) PLASMONIC NON-DISPERSIVE INFRARED GAS SENSORS

(71) Applicant: International Business Machines Corporation, Armonk, NY (US)

(72) Inventors: Abram L. Falk, Port Chester, NY (US); Damon B. Farmer, White Plains, NY (US); Shu-Jen Han, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/918,638

(22) Filed: Mar. 12, 2018

(65) Prior Publication Data

US 2019/0277761 A1   Sep. 12, 2019

(51) Int. Cl.
*G01N 21/552* (2014.01)
*G01N 21/3504* (2014.01)

(52) U.S. Cl.
CPC ....... *G01N 21/554* (2013.01); *G01N 21/3504* (2013.01)

(58) Field of Classification Search
CPC ................. G01N 21/554; G01N 21/3504
USPC ........................................................ 356/409
See application file for complete search history.

(56) References Cited

U.S. PATENT DOCUMENTS

| 5,077,469 | A | 12/1991 | Fabinski et al. |
| 5,313,264 | A | 5/1994 | Ivarsson et al. |
| 5,886,348 | A | 3/1999 | Lessure et al. |
| 7,376,403 | B1 * | 5/2008 | Wanke ................. H01L 29/205 257/19 |
| 8,471,208 | B1 | 6/2013 | Tang |
| 9,117,722 | B1 * | 8/2015 | Koenck .............. H01L 31/1868 |
| 9,423,345 | B2 | 8/2016 | Avouris et al. |
| 2012/0134880 | A1 | 5/2012 | Kurkina et al. |
| 2015/0260668 | A1 | 9/2015 | Alam et al. |
| 2018/0202993 | A1 * | 7/2018 | Molina ................ A61B 5/4836 |
| 2019/0137341 | A1 * | 5/2019 | Afzali-Ardakani ..... G01J 5/046 |

OTHER PUBLICATIONS

Wang et al. ("Nanopin Plasmonic Resonator Array and Its Optical Properties", Nano Letters, vol. No. 4, 2007, pp. 1076-1080) (Year: 2007).*

(Continued)

*Primary Examiner* — Hina F Ayub
(74) *Attorney, Agent, or Firm* — Vazken Alexanian; Michael J. Chang, LLC (57) ABSTRACT

Differential, plasmonic, non-dispersive infrared gas sensors are provided. In one aspect, a gas sensor includes: a plasmonic resonance detector including a differential plasmon resonator array that is resonant at different wavelengths of light; and a light source incident on the plasmonic resonance detector. The differential plasmon resonator array can include: at least one first set of plasmonic resonators interwoven with at least one second set of plasmonic resonators, wherein the at least one first set of plasmonic resonators is configured to be resonant with light at a first wavelength, and wherein the at least one second set of plasmonic resonators is configured to be resonant with light at a second wavelength. A method for analyzing a target gas and a method for forming a plasmonic resonance detector are also provided.

14 Claims, 11 Drawing Sheets

(56) References Cited

OTHER PUBLICATIONS

Bates et al., "Evaluating Infrared Carbon Dioxide Sensors for 21st Century Cell Culture: introducing the Thermo Scientific IR180S1 Infrared CO2 sensor," Thermo Scientific, 2014 (downloaded Dec. 13, 2017) (5 total pages).
Chiu et al., "Strong and Broadly Tunable Plasmon Resonances in Thick Films of Aligned Carbon Nanotubes," Nano Letters, 2017, 17, pp. 5641-5645 (Aug. 2017).
Chiu et al. "Strong and Broadly Tunable Plasmon Resonances in Thick Films of Aligned Carbon Nanotubes," Nano Letters, 2017, 17 (Aug. 2017) Supporting Information (6 total pages).
Martin-Moreno et al., "Ultraefficient Coupling of a Quantum Emitter to the Tunable Guided Plasmons of a Carbon Nanotube," Physical Review Letters, 115, 173601 (2015) (5 total pages).
J. Hone et al., "Thermoelectric Power of Single-Walled Carbon Nanotubes," Phys. Rev. Lett. 80, pp. 1042-1045 (Feb. 1998).

* cited by examiner

PLASMONIC NON-DISPERSIVE INFRARED GAS SENSORS

FIELD OF THE INVENTION

The present invention relates to gas sensors, and more particularly, to differential plasmonic, non-dispersive infrared gas sensors.

BACKGROUND OF THE INVENTION

Most compact carbon dioxide ($CO_2$) sensors are based on non-(optically) dispersive infrared detection (NDIR). $CO_2$ has a strong infrared (IR) absorption peak at a wavelength of 4.3 micrometers ($\mu m$), which is well-isolated from those of other gases in the ambient air. In the simplest type of NDIR spectrometer, an incandescent light source passes through a volume of $CO_2$ gas, through a 4.3 $\mu m$ filter, and to a mid-infrared receiver, which is typically a thermopile. See, for example, FIG. 1 in Bates et al., "Evaluating Infrared Carbon Dioxide Sensors for $21^{st}$ Century Cell Culture: introducing the Thermo Scientific IR180S1 Infrared $CO_2$ sensor," Thermo Scientific, 2014 (downloaded Dec. 13, 2017) (5 total pages) (hereafter "Bates"), the contents of which are incorporated by reference as if fully set forth herein. The inferred $CO_2$ concentration is directly proportional to the absorption of the 4.3 $\mu m$ light. See Bates.

Drift is the largest source of inaccuracy in NDIR $CO_2$ sensors. Drift is caused by a variety of factors, including the incandescent light source slowly burning out, the thermopile responsivities drifting, dust and dirt accumulating within the optical path, and the ambient humidity level changing. Drift is also intertwined with the size and energy-use profile of the sensor because, all other things being equal, a more accurate $CO_2$ sensor can use a less intense light source and/or a smaller optical path length.

To correct for drift, a wavelength slightly removed from the 4.3 $\mu m$ $CO_2$ absorption peak (such as 4.0 $\mu m$) can be used as a reference. One way to measure the second wavelength is to use a dispersive filter (see, for example, FIG. 2 of Bates), which splits the incandescent light into multiple wavelengths. However, in this configuration, the signal and reference detectors can be subject to one of the detectors selectively drifting (e.g., by dust accumulating on one of them).

Thus, improved NDIR gas sensor designs would be desirable.

SUMMARY OF THE INVENTION

The present invention provides differential, plasmonic, non-dispersive infrared gas sensors. In one aspect of the invention, a gas sensor is provided. The gas sensor includes: a plasmonic resonance detector including a differential plasmon resonator array that is resonant at different wavelengths of light; and a light source incident on the plasmonic resonance detector. The differential plasmon resonator array can include: at least one first set of plasmonic resonators interwoven with at least one second set of plasmonic resonators, wherein the at least one first set of plasmonic resonators is configured to be resonant with light at a first wavelength, and wherein the at least one second set of plasmonic resonators is configured to be resonant with light at a second wavelength.

In another aspect of the invention, a method for analyzing a target gas is provided. The method includes: illuminating the target gas with light from a light source, wherein the light is incident on a plasmonic resonance detector including a differential plasmon resonator array having at least one first set of plasmonic resonators interwoven with at least one second set of plasmonic resonators, wherein the at least one first set of plasmonic resonators is configured to be resonant with the light at a first wavelength corresponding to a peak absorption wavelength of the target gas, and wherein the at least one second set of plasmonic resonators is configured to be resonant with the light at a second wavelength corresponding to a reference wavelength; absorbing the light by the at least one first set of plasmonic resonators and the at least one second set of plasmonic resonators, wherein the light at the first wavelength incident on the at least one first set of plasmonic resonators is dependent on an amount of the light at the first wavelength absorbed by the target gas; generating a photocurrent signal $I_1$ in the at least one first set of plasmonic resonators and a photocurrent signal $I_2$ in the at least one second set of plasmonic resonators; and determining a concentration of the target gas using $I_1-I_2$.

In yet another aspect of the invention, a method for forming a plasmonic resonance detector is provided. The method includes: forming at least one first set of plasmonic resonators interwoven with at least one second set of plasmonic resonators, wherein the at least one first set of plasmonic resonators is configured to be resonant with light at a first wavelength corresponding to a peak absorption wavelength of the target gas, and wherein the at least one second set of plasmonic resonators is configured to be resonant with light at a second wavelength corresponding to a reference wavelength.

A more complete understanding of the present invention, as well as further features and advantages of the present invention, will be obtained by reference to the following detailed description and drawings.

DETAILED DESCRIPTION OF PREFERRED EMBODIMENTS

Provided herein are gas sensors having wavelength-selective 'filters' built into the detectors, by using resonant detectors that selectively absorb only certain wavelengths of light. See, for example, gas sensor 100 in FIG. 1. Gas sensor 100 includes a light source 102 and a plasmonic resonance detector array 104 both housed within an enclosure 101. Enclosure 101 is air-tight except for an air inlet 101a and an air outlet 101b, configured to permit an air sample to enter and exit the enclosure 101, respectively. Air introduced to the enclosure 101 via air inlet 101a can simply passively diffuse through the enclosure 101, or a fan (not shown) can draw it through.

Figure 1:
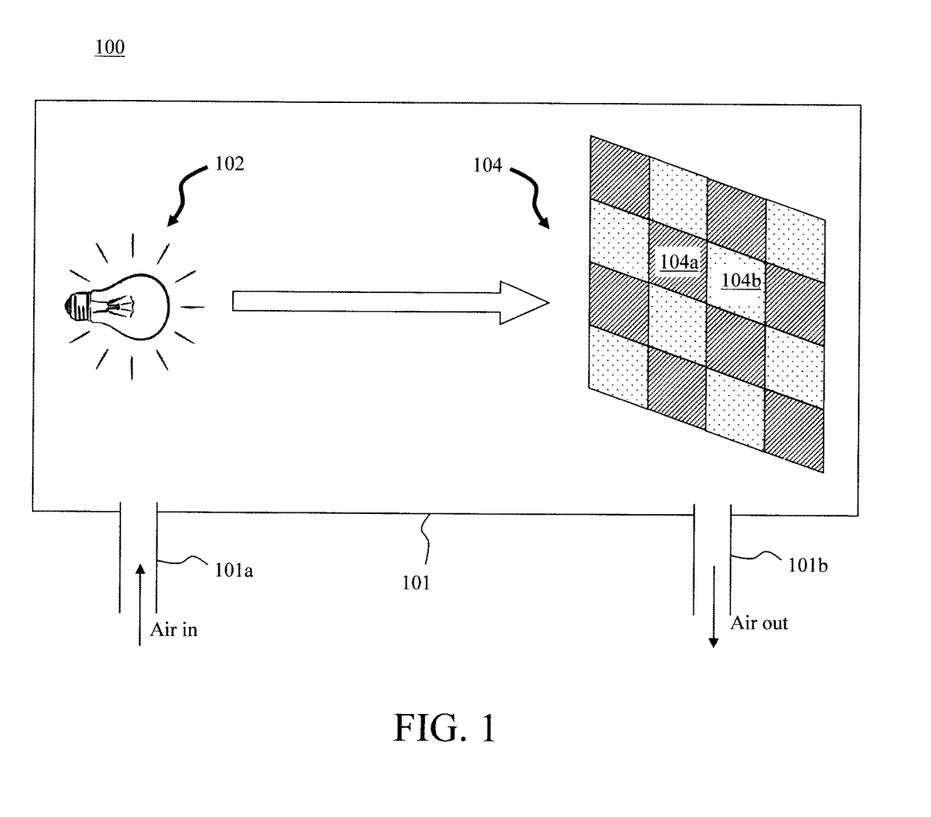
FIG. 1 is a diagram illustrating an exemplary plasmonic, non-dispersive infrared gas sensor according to an embodiment of the present invention.

According to one exemplary embodiment, the light source 102 is an incandescent light bulb that is incident on the plasmonic resonance detector 104. The plasmonic resonance detector 104 includes an array of plasmon resonators as absorbers. The array includes at least two different types of plasmon resonators. For instance, as shown in FIG. 1 the plasmonic resonance detector 104 includes (a first set of) resonators 104a and (a second set of) resonators 104b that are resonant at different wavelengths of light. For ease and clarity of description, reference will be made herein to the first resonators 104a being resonant at a first wavelength of light and the second resonators 104b being resonant at a second wavelength of light. For instance, by way of example only, the resonators 104a in plasmonic resonance detector 104 could be resonant at 4.3 micrometers ($\mu m$), the vibrational resonance of carbon dioxide ($CO_2$), and the resonators 104b in plasmonic resonance detector 104 could provide a differential signal by absorbing 4.0 $\mu m$ light which can be used as a reference, e.g., to correct for drift. Thus, the reference wavelength used is slightly removed from the target gas absorption peak. The shift of the reference detector should be spaced away from the signal detector by approximately f/Q, wherein f is the frequency of the vibrational resonance being detected (i.e., 4.3 $\mu m$ for the case of $CO_2$), and Q is the quality factor of the resonator. For the case of carbon nanotube resonators, Q is approximately 10 (see Chiu et al, Nano Lett)), so 4.0 $\mu m$ is an appropriate reference frequency. See, for example, Chiu et al., "Strong and Broadly Tunable Plasmon Resonances in Thick Films of Aligned Carbon Nanotubes," Nano Letters, 2017, 17, pgs. 5641-5645 (August 2017) (hereinafter "Chiu"), the contents of which are incorporated by reference as if fully set forth herein. If the reference frequency is too close to the target gas absorption peak, the two detectors will experience crosstalk. If it is too far away, the reference detector may experience different sources of drift from the signal detector.

Figure 2:
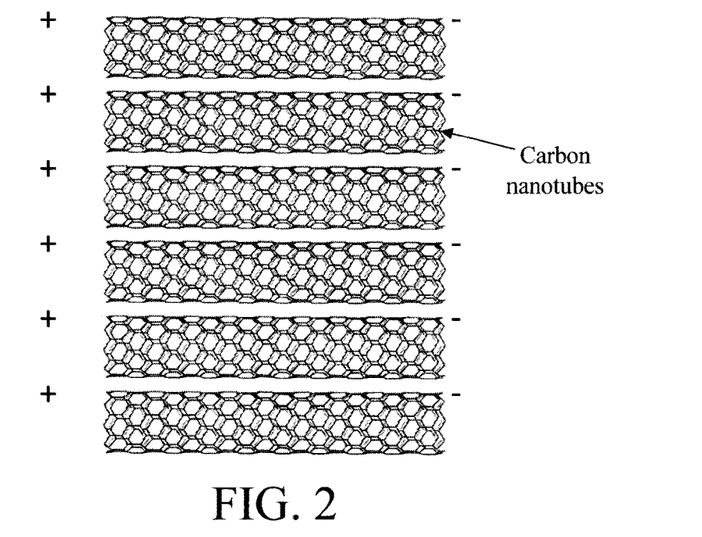
FIG. 2 is a schematic diagram illustrating plasmons in carbon nanotubes according to an embodiment of the present invention.

According to one exemplary embodiment, the physical basis of these resonant absorbers is the excitation of plasmons in carbon nanotubes. These plasmons comprise longitudinal charge oscillations that are bound by the carbon nanotube ends (see FIG. 2) coupled to infrared optical fields, which can concentrate light into nanoscale volumes. See, for example, Chiu.

Carbon nanotubes are an exemplary plasmonic material. See, for example, Martin-Moreno et al., "Ultraefficient Coupling of a Quantum Emitter to the Tunable Guided Plasmons of a Carbon Nanotube," Physical Review Letters, 115, 173601 (2015) (5 total pages), the contents of which are incorporated by reference as if fully set forth herein. Carbon nanotubes are an excellent photothermoelectric material, producing a strong photocurrent or photovoltage in response to light. Their plasmon resonances are also confined, meaning that the size of a carbon nanotube plasmon resonator can be much shorter (approximately 50 times smaller) than the free-space wavelength of light that it is detecting. Carbon nanotubes are also highly tunable via the size of the nanotubes involved in the resonator and the doping level of the nanotubes, allowing them to span frequencies from the terahertz up to the near infrared.

Figure 3:
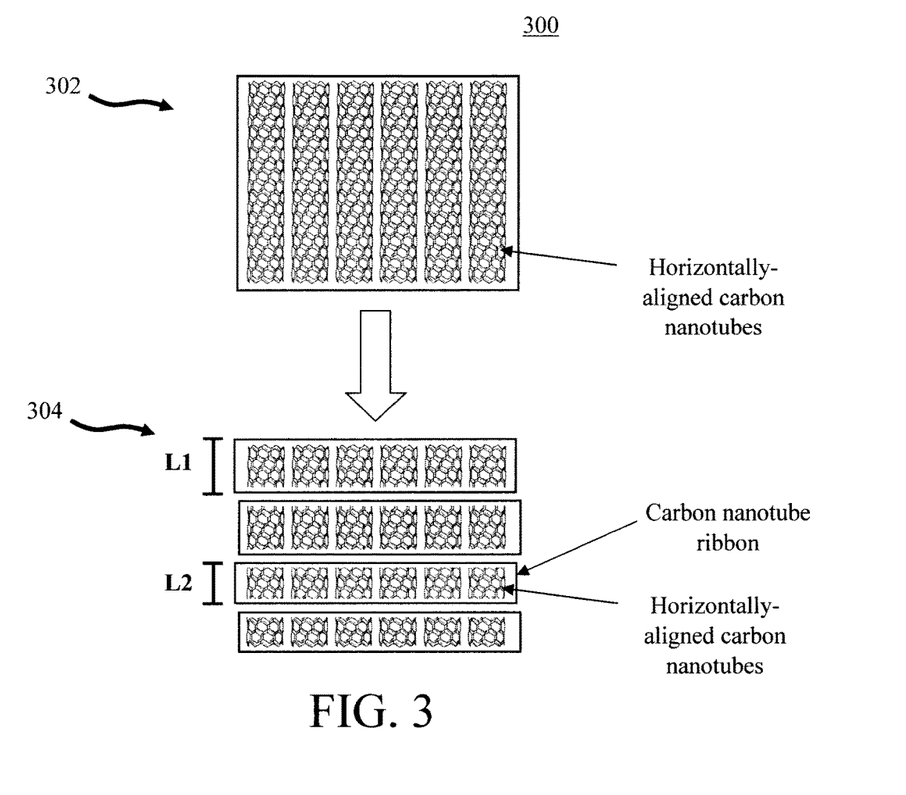
FIG. 3 is a diagram illustrating an exemplary methodology for processing carbon nanotubes according to an embodiment of the present invention.

According to an exemplary embodiment, the carbon nanotubes are processed into ribbons that are cut to at least two different lengths L1 and L2. See, for example, FIG. 3 which illustrates an exemplary methodology 300 for processing carbon nanotubes. Specifically, as shown in step 302 carbon nanotubes are aligned horizontally into sheets. In step 304, the sheets are then etched into ribbons, i.e., strips cut/etched from the sheets containing the horizontally-aligned carbon nanotubes cut to different lengths. In this example, the ribbons/carbon nanotubes in the ribbons are etched to two different lengths, L1 and L2 wherein L1>L2.

Figure 4:
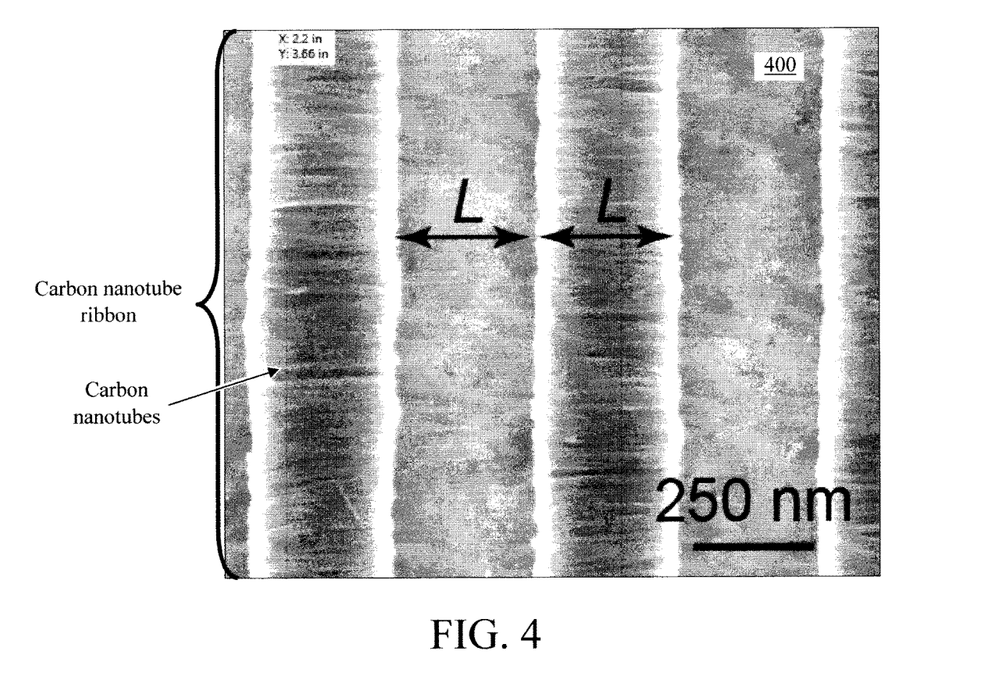
FIG. 4 is a scanning electron micrograph (SEM) image of ribbons of carbon nanotubes according to an embodiment of the present invention.

FIG. 4 is a scanning electron micrograph (SEM) image 400 of ribbons of carbon nanotubes (i.e., the vertical stripes in image 400) each having aligned carbon nanotubes etched to a length L. Note that the orientation of the carbon nanotubes/ribbons in image 400 is rotated 90° from what is depicted, for example, in step 304 of FIG. 3.

Figure 5:
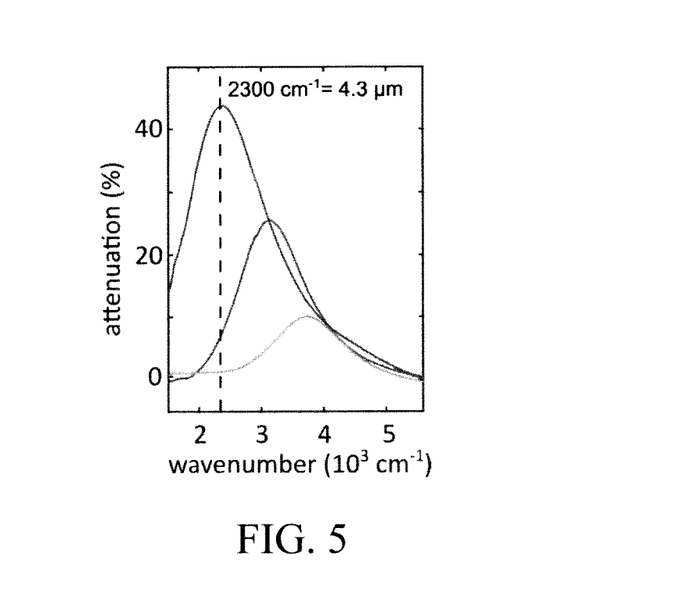
FIG. 5 is a diagram illustrating the absorption spectra from three different ribbons of carbon nanotubes having different lengths according to an embodiment of the present invention.

As highlighted above, these nanotube assemblies function as plasmon resonators. Etching the carbon nanotubes to different lengths gives them different resonance wavelengths. See, for example, FIG. 5 which illustrates the absorption spectra from three different ribbons of carbon nanotubes having different lengths. As demonstrated in FIG. 5, this technique of tailoring the resonance via the carbon nanotube length is effective in overlapping the spectrum of the carbon nanotubes with that of $CO_2$ (2300 $cm^{-1}$, equivalent to a wavelength of 4.3 mm). In FIG. 5, the lengths of the three carbon nanotube plasmon resonators whose attenuation spectra is shown are, from lowest to highest energies, 1 $\mu m$, 600 nanometers (nm), and 300 nm.

After they are etched (e.g., into ribbons), the carbon nanotubes function as Fabry-Perot resonators for light. The resonance frequencies of the etched carbon nanotube ribbons (also referred to herein as "nanoribbons") are proportional to the square root of the free charge density on the carbon nanotubes×a thickness of the ribbon (i.e., out of the plane) divided by the carbon nanotube length (L—see FIG.

4, described above). Using this relationship, one skilled in the art given the present teachings could tailor the carbon nanotube length to a particular plasmon resonance frequency for a given gas sensing application.

As provided above, in the present gas sensor designs, the conventional filter and thermopile is replaced with a plasmonic resonance detector (see, for example, plasmonic resonance detector 104 in FIG. 1) having at least a first set of plasmonic resonators (e.g., resonators 104a in FIG. 1) being resonant at a first wavelength of light and at least one second set of resonators (e.g., resonators 104b) being resonant at a second wavelength of light. For instance, the first set of resonators can be resonant at a wavelength corresponding to the absorption peak of a target gas (such as $CO_2$), while the second set of resonators is resonant at a different wavelength, i.e., providing a differential signal, e.g., to correct for drift. An exemplary configuration of the present plasmonic resonance detector using ribbons of carbon nanotubes having different lengths as the first/second regions is shown illustrated in FIG. 6. Specifically, plasmonic resonance detector 600 shown in FIG. 6 includes (first and second sets of) ribbons 602a and 602b of carbon nanotubes having at least two different lengths, e.g., lengths L1 and L2—respectively, whereby the ribbons 602a of carbon nanotubes having the first length L1 correspond to the first regions resonant at the first wavelength, and the ribbons 602b of carbon nanotubes having the second length L2 correspond to the second regions resonant at the second wavelength.

According to an exemplary embodiment, the first regions are resonant at the absorption peak of a target gas, and the second regions provide a differential signal at a slightly different wavelength, or vice versa. For instance, by way of example only, for L1 the plasmon resonance of the carbon nanotubes is tuned to be 4.3 μm, to measure the $CO_2$ absorption signal ($I_{4.3}$), and L2 is tuned to have a resonance at 4.0 μm, so as to provide a reference ($I_{4.0}$). The difference between the two signals, differential signal $I_{4.3}-I_{4.0}$, is directly proportional to the concentration of $CO_2$ in the optical path (i.e., between the light source and the carbon nanotube plasmonic resonance detector array—see for example FIG. 7, described below).

Figure 6:
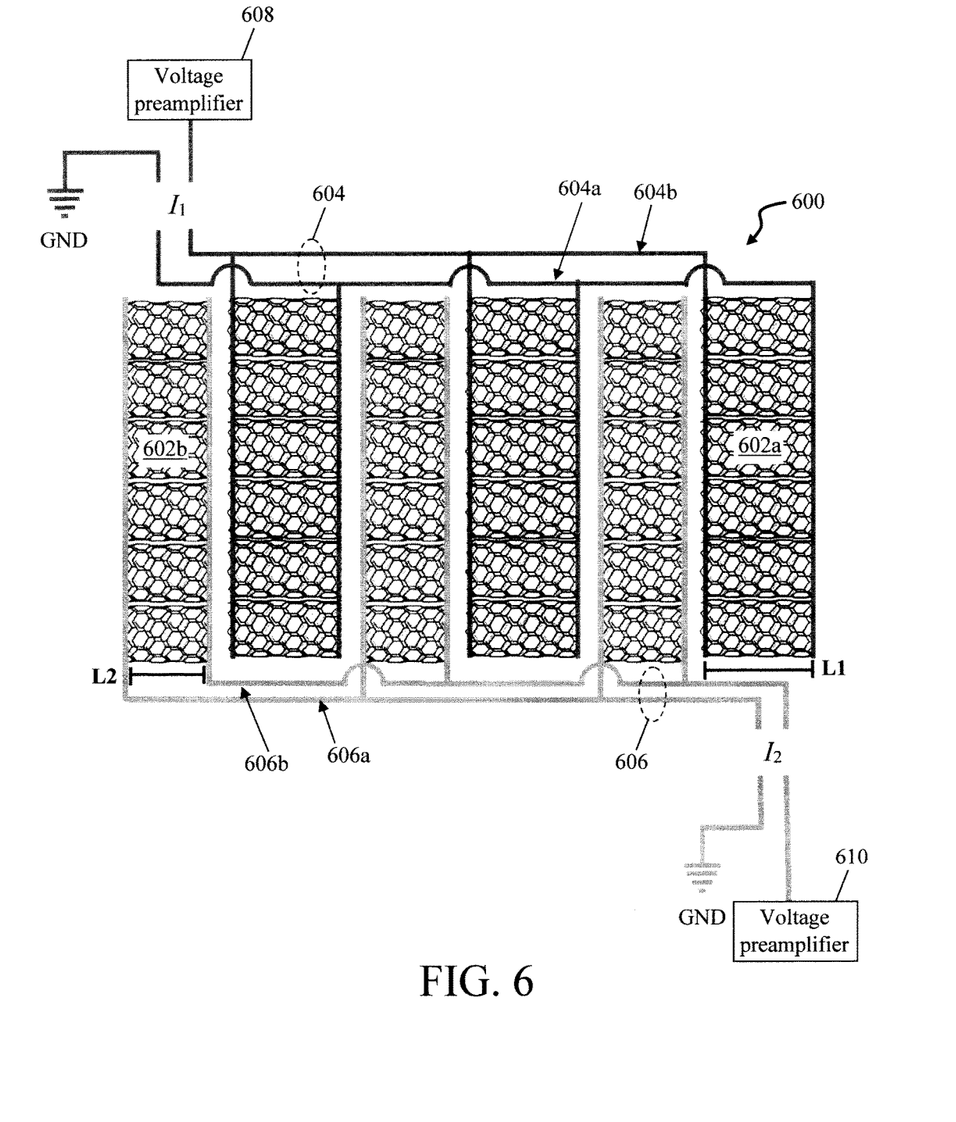
FIG. 6 is a diagram illustrating an exemplary configuration of the present plasmonic resonance detector using carbon nanotubes according to an embodiment of the present invention.

As shown in FIG. 6, (first and second) metal contacts 604 and 606 are formed to the ribbons 602a and 602b of carbon nanotubes, respectively. Specifically, the metal contacts 604 are formed contacting the carbon nanotubes (having length L1) in ribbon 602a, and the metal contacts 606 are formed contacting the carbon nanotubes (having length L2) in ribbon 602b. The metal contacts 604 and 606 are used to extract the target gas absorption signal ($I_1$) and the reference signal ($I_2$) from the ribbons 602a and 602b of carbon nanotubes, respectively. For instance, in the non-limiting example provided above, the metal contacts 604 are used to extract the $CO_2$ absorption signal ($I_{4.3}$), and the metal contacts 606 are used to extract the reference signal ($I_{4.0}$).

According to an exemplary embodiment, one contact to each resonator is grounded while the other is connected (through wirebonds, chip carriers, etc.—not shown) to a voltage preamplifier, which will convert the photovoltage to a macroscopic voltage that can be outputted. Specifically, as shown in FIG. 6, metal contacts 604 to carbon nanotube the ribbons 602a (i.e., the target gas signal resonators) include a first contact 604a which is grounded and a second contact 604b that is connected to a voltage preamplifier 608. Likewise, metal contacts 606 to carbon nanotube the ribbons 602b (i.e., the reference signal resonators) include a first contact 606a which is grounded and a second contact 606b that is connected to a voltage preamplifier 610.

The present gas sensor has several advantages over traditional designs that use separated filters and detectors. First, the spatial pattern of the resonant detectors can be interwoven, so that the effects of macroscopic mechanical drift and dust are minimized. See, for example, FIG. 1 where the first and second resonators 104a and 104b are interwoven in plasmonic resonance detector 104, and FIG. 6 where the carbon nanotube ribbons 602a and 602b (i.e., the resonant detectors) are interwoven in plasmonic resonance detector 600. Second, the resonant detectors are more efficient at harvesting the energy at their absorption peak, because the presence of resonance enhances the absorption of light. In turn, this efficiency allows the light source to be less bright, and less power to be consumed by the overall detector. Third, additional wavelengths can easily be added to the sensor, for sensing other gases like carbon monoxide. Finally, the simpler design of the overall sensor, with an integrated filter and detector, can lead to more flexible opportunities for deployment.

Figure 7:
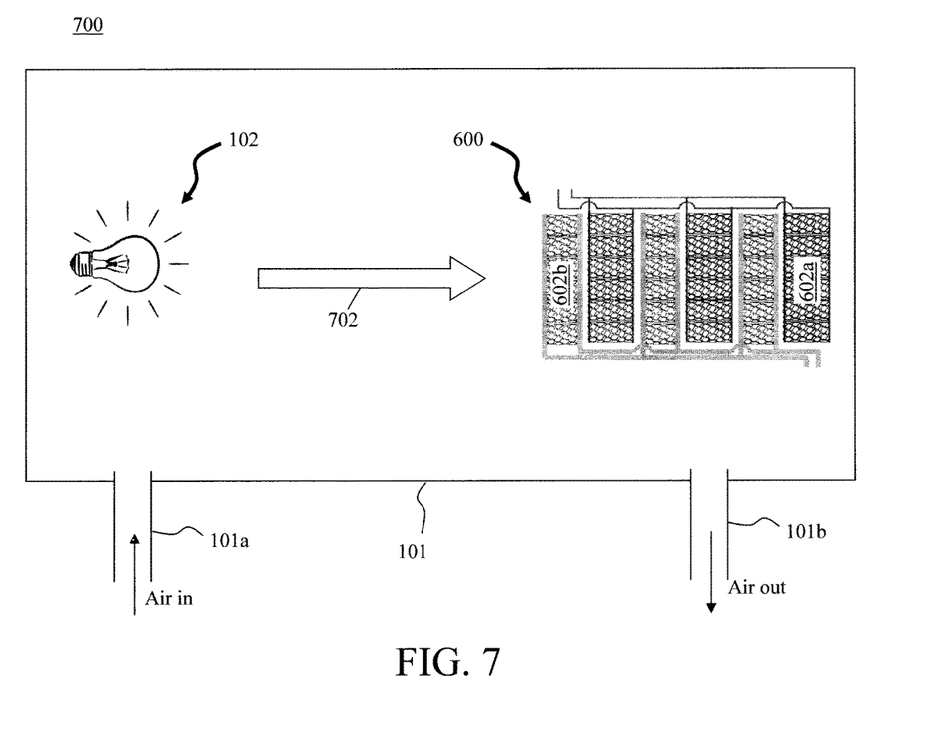
FIG. 7 is a diagram illustrating an exemplary gas sensor employing the carbon nanotube plasmonic resonance detector of FIG. 6 according to an embodiment of the present invention.

FIG. 7 is a diagram illustrating an exemplary gas sensor 700 employing carbon nanotube plasmonic resonance detector 600 (of FIG. 6). In this example, the same set-up is used as in FIG. 1, except that the plasmonic resonance detector array 104 is configured as described in conjunction with the description of FIG. 6 above, i.e., having resonant detectors formed from ribbons of carbon nanotubes of differing lengths. Like structures are numbered alike in the figures. Arrow 702 is used to indicate the optical path between the light source 102 and the plasmonic resonance detector 600.

Figure 8:
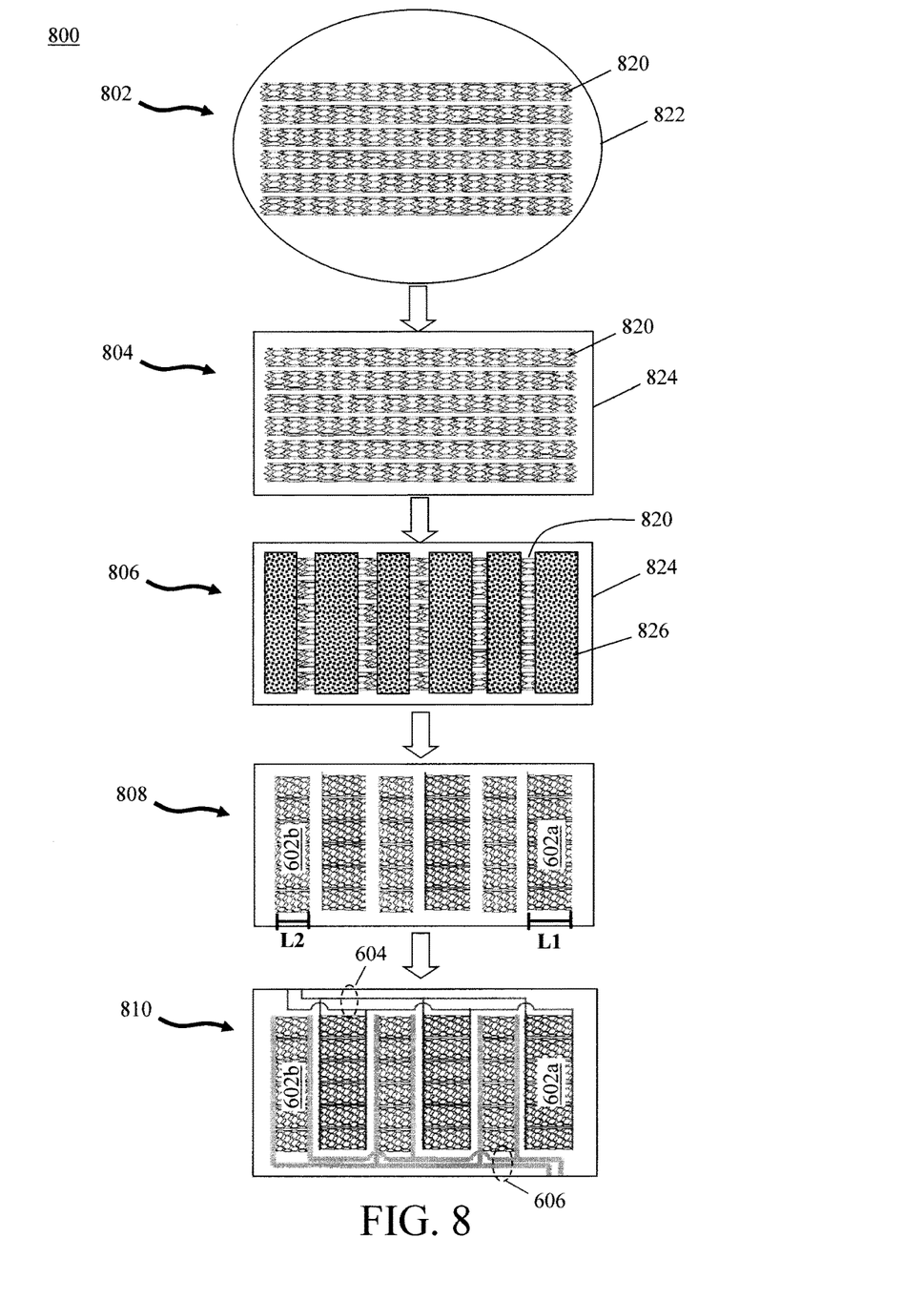
FIG. 8 is a diagram illustrating an exemplary methodology for forming the plasmonic resonance detector of FIG. 6 according to an embodiment of the present invention.

An exemplary methodology 800 for forming plasmonic resonance detector 600 (of FIG. 6) is now described by way of reference to FIG. 8. In step 802, thick films of aligned carbon nanotubes 820 are deposited onto a filter membrane 822 using a vacuum filtration technique. See, for example, Chiu and Supporting Information for Chiu et al. "Strong and Broadly Tunable Plasmon Resonances in Thick Films of Aligned Carbon Nanotubes," Nano Letters, 2017, 17 (August 2017) (6 total pages) (hereinafter "Supporting Information for Chiu"), the contents of both of which are incorporated by reference as if fully set forth herein. For instance, single-walled carbon nanotubes are first dispersed in an aqueous solution with a surfactant, e.g., sodium dodecylbenesulfonate (SDBS), and the dispersion is slowly vacuum-filtered onto a filtration membrane such as a polycarbonate filter membrane. If the filtration speed and surfactant concentration is optimized, this process results in aligned films of carbon nanotubes. See Chiu and Supporting Information for Chiu.

In step 804, the aligned carbon nanotubes 820 are then transferred from the filter membrane 822 to an insulating substrate 824. According to an exemplary embodiment, the insulating substrate 824 includes, but is not limited to, high-resistivity silicon (Si), plastic, and glass. In another exemplary embodiment, the insulating substrate 824 includes an insulating layer (on which the detector is formed) over a semiconductor. For instance, by way of example only, the insulating substrate 824 can include a bulk semiconductor (e.g., Si, germanium (Ge), silicon germanium (SiGe), III-V, etc.) wafer covered with a dielectric such as silicon dioxide ($SiO_2$), hafnium oxide ($HfO_2$) and/or aluminum oxide ($Al_2O_3$). Use of a semiconductor under the insulator enables the implementation of electronics in the semiconductor (e.g., detector readout electronics and signal processing) that support the detector.

According to an exemplary embodiment, the aligned carbon nanotubes 820 are transferred to the semiconductor substrate 824 by etching the filter membrane 822. See, for example, Chiu and Supporting Information for Chiu. Namely, the filter membrane 822 is placed face down on the substrate 824 with the aligned carbon nanotubes 820 in direct contact with the dielectric. Pressing the filter membrane 822 onto the substrate 824 (e.g., via a glass slide placed over the filter membrane 822) can be used to adhere the aligned carbon nanotubes 820 onto the substrate 824. An organic solvent is then used to dissolve the filter membrane 822, leaving behind the aligned carbon nanotubes 820 on the substrate 824 as shown in step 804. Suitable organic solvents include, but are not limited to, N-methyl-2-pyrrolidone and/or chloroform.

In step 806, a patterned mask 826 is then formed over the aligned carbon nanotubes 820. The mask 826 can include a standard hardmask material such as silicon nitride (SiN) patterned using standard optical lithography and etching techniques or, as described in Chiu, a poly(methyl methacrylate)/hydrogen silsesquioxane (PMMA/HSQ) mask patterned using electron beam (e-beam) lithography. The mask 826 marks the footprint and location of the ribbons of (horizontally-aligned) carbon nanotubes having different lengths. According to an exemplary embodiment, the mask 826 defines carbon nanotubes having at least two lengths, L1 and L2—see above. By way of example only, as described above, L1 can correspond to the 4.3 μm $CO_2$ absorption and L2 to the 4.0 μm reference.

In step 808, an etch is used to transfer the mask 826 to the aligned carbon nanotubes 820, patterning the film of aligned carbon nanotubes 820 into ribbons of carbon nanotubes having at least two different lengths. For instance, in the example shown in FIG. 8, the aligned carbon nanotubes 820 are patterned into ribbons 602a and 602b of carbon nanotubes having two lengths L1 and L2, wherein L1>L2. By way of example only, as provided above, L1 can correspond to the 4.3 μm $CO_2$ absorption and L2 to the 4.0 μm reference. Suitable etching processes include, but are not limited to, reactive ion etching (RIE) in a plasma such as oxygen plasma. Following the nanoribbon etch, any remaining mask 826 can be removed.

Finally, in step 810 metal contacts 604 and 606 are formed to the ribbons 602a and 602b of carbon nanotubes, respectively. Standard metallization techniques can be employed. Suitable contact metals include, but are not limited to, copper (Cu), nickel (Ni), platinum (Pt) and/or palladium (Pd).

Figure 9:
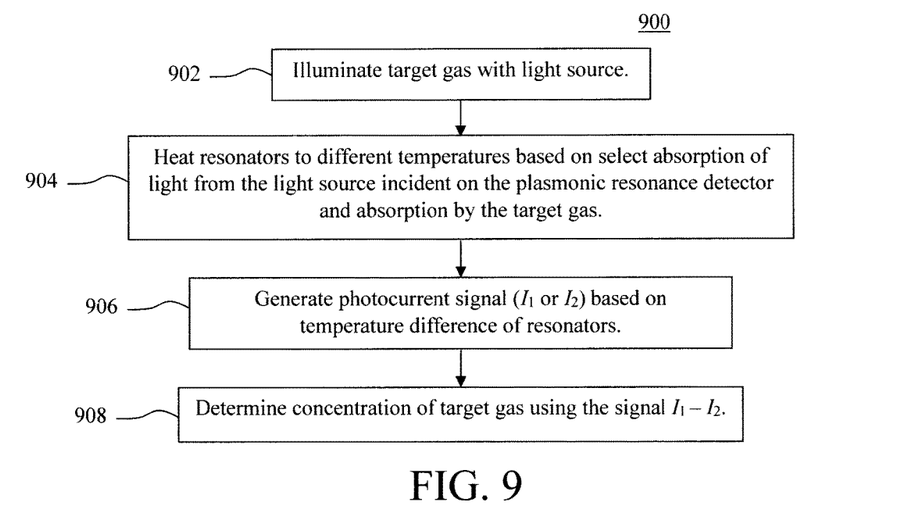
FIG. 9 is a diagram illustrating an exemplary methodology for gas detection using the present plasmonic, non-dispersive infrared gas sensors according to an embodiment of the present invention.

An exemplary methodology 900 for analyzing a target gas using the present plasmonic resonance gas sensors is now described by way of reference to FIG. 9. The description of methodology 900 will use the design of gas sensor 100 (of FIG. 1) as a general reference point and, where appropriate, incorporate features of the various other embodiments described herein.

In step 902, a light source (e.g., light source 102) is used to illuminate the target gas within the enclosure 101. According to an exemplary embodiment, the light source is an incandescent light source that is incident on the plasmonic resonance detector 104 as in FIG. 1 or the plasmonic resonance detector 600 as in FIG. 6. In that case, gas within the enclosure 101 will cross the optical path between the light source and the plasmonic resonance detector. Alternative light sources are also described herein. For instance, a plasmonic light source is described in conjunction with the description of FIG. 10 below, which generates quasi-coherent light.

The target gas absorbs a specific wavelength of infrared light from the light source. By way of example only, as provided above, $CO_2$ has an absorption peak at 4.3 μm. As also provided above, the plasmonic resonance detector includes at least two different resonators, one resonant at the absorption peak of the target gas and the other resonant at a reference wavelength (e.g., a 4.0 μm reference for 4.3 μm $CO_2$ absorption). See, for example, first regions 104a and second regions 104b of plasmonic resonance detector 104. For instance, in the case of a carbon nanotube-based plasmonic resonance detector such as detector 600 in FIG. 6, the carbon nanotubes are etched to at least two different lengths (e.g., L1 and L2) corresponding to different plasmon resonances in the carbon nanotubes, one at the absorption peak of the target gas and the other at a reference wavelength. Embodiments will also be provided below with plasmonic resonance detectors that employ different sized non-carbon nanotube resonators.

The notion here is that the resonators are configured (e.g., by their size/length) to resonate either at the same wavelength as the target gas or at a reference wavelength. Light from the light source will be absorbed by the resonators, causing the resonators to be heated and thereby generate photocurrent signals $I_1$ and $I_2$ (see above) via photothermoelectric effects. When the target gas is present in the enclosure 101 in between the light source and the plasmonic resonance detector, the target gas will also absorb that same wavelength of infrared light from the light source, with the amount of absorption being proportional to the concentration of the target gas. Thus, the amount of light of that target wavelength incident on the resonators will be based on how much has already been absorbed by the target gas. The reference signal remains unchanged by the target gas. As such, the difference in the photocurrent signals $I_1$ and $I_2$ (e.g., target gas and reference signals, respectively), i.e., $I_1-I_2$, will indicate an amount of the target gas in the enclosure 101. Further, a reading of $I_1$ and $I_2$ without the target gas present can be used to establish a baseline reading of $I_1-I_2$ for comparison.

Namely, in step 904 the selective absorption of light by the (different sized) resonators (e.g., L1 and L2 in the case of carbon nanotube-based plasmonic resonance detector 600 of FIG. 6) causes the resonators to be heated to different temperatures, for example, a temp1 and a temp2. As provided above, the amount of light at the target wavelength incident on the resonators is dependent on an amount of the light at the target wavelength already absorbed by the target gas. Due to the Seebeck effect, in step 906, a voltage is induced across the resonators, generating a photocurrent ($I_1$ or $I_2$) via photothermoelectric transduction. A description of the strong thermoelectric effect in carbon nanotubes is provided in J. Hone et al., "Thermoelectric Power of Single-Walled Carbon Nanotubes," Phys. Rev. Lett. 80, pgs. 1042-1045 (February 1998), the contents of which are incorporated by reference as if fully set forth herein. In step 908, the signal $I_1-I_2$ is used to determine the concentration of the target gas in the enclosure.

To use the above-described example of $CO_2$ detection to further illustrate this concept, assume that the resonators are configured to resonate at 4.3 μm (corresponding to the peak absorption of the target gas $CO_2$) and 4.0 μm (as a reference). Without any $CO_2$ the signal from these resonators, i.e., $I_{4.3}-I_{4.0}$, will have a certain value x. However, when $CO_2$ is present in the enclosure 101 in the light path between the light source and the plasmonic resonance detector, its absorption at 4.3 μm will decrease an amount of infrared light at 4.3 μm incident upon the plasmonic resonance detector, thereby changing the photocurrent signal $I_{4.3}$ and output value x. The amount by which $I_{4.3}$ is changed is proportional to the concentration of $CO_2$ in the enclosure 101 (since a larger concentration of the $CO_2$ absorbs more light at 4.3 µm, and vice versa). Namely, the amount by which output value x changes is proportional to the concentration of the target gas $CO_2$.

Figure 10:
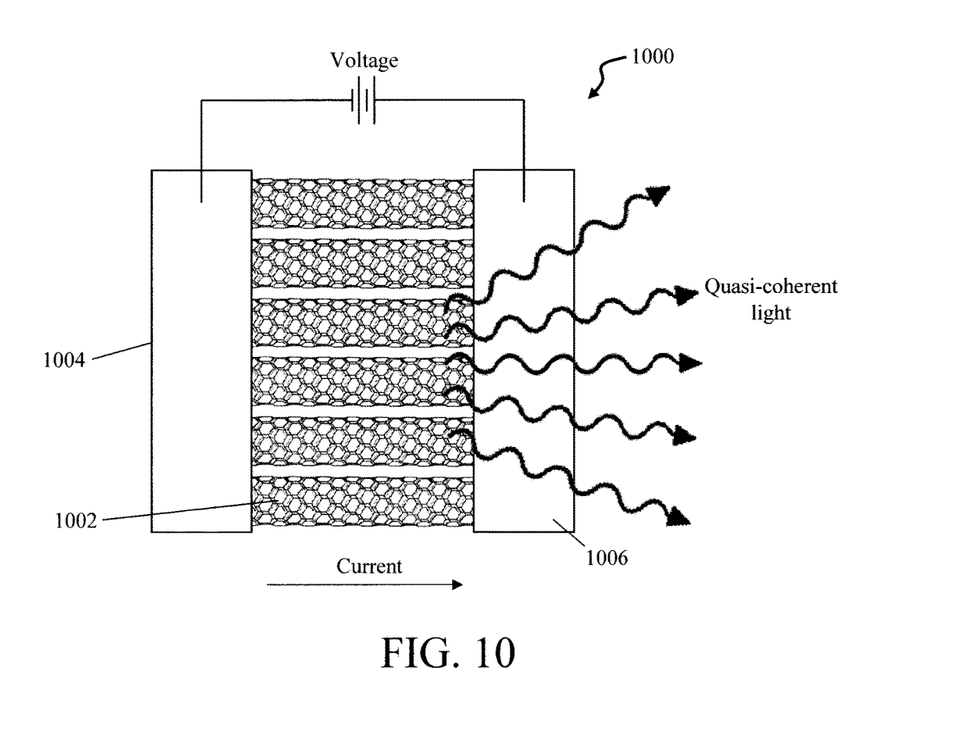
FIG. 10 is a diagram illustrating an exemplary plasmonic light source according to an embodiment of the present invention.

As highlighted above, light sources other than an incandescent light bulb are also contemplated herein. For instance, according to an alternative embodiment, a plasmonic light source is employed in the present gas sensor design. See, for example, FIG. 10. As shown in FIG. 10 plasmonic light source 1000 includes a plurality of plasmonic resonators (in this case aligned carbon nanotubes 1002) in between (first and second) electrodes 1004 and 1006. As shown in FIG. 10, a voltage source (labeled "Voltage") applies a voltage across the electrodes 1004 and 1006 causing current to pass through the plasmonic resonators, i.e., carbon nanotubes 1002. This causes the carbon nanotubes 1002 to heat up and emit quasi-coherent light via thermal ("blackbody") radiation. In this case, the wavelength of the emitted light will be modified from the blackbody spectrum via the Purcell effect to be concentrated at the center wavelength of the resonators of the light source.

Figure 11:
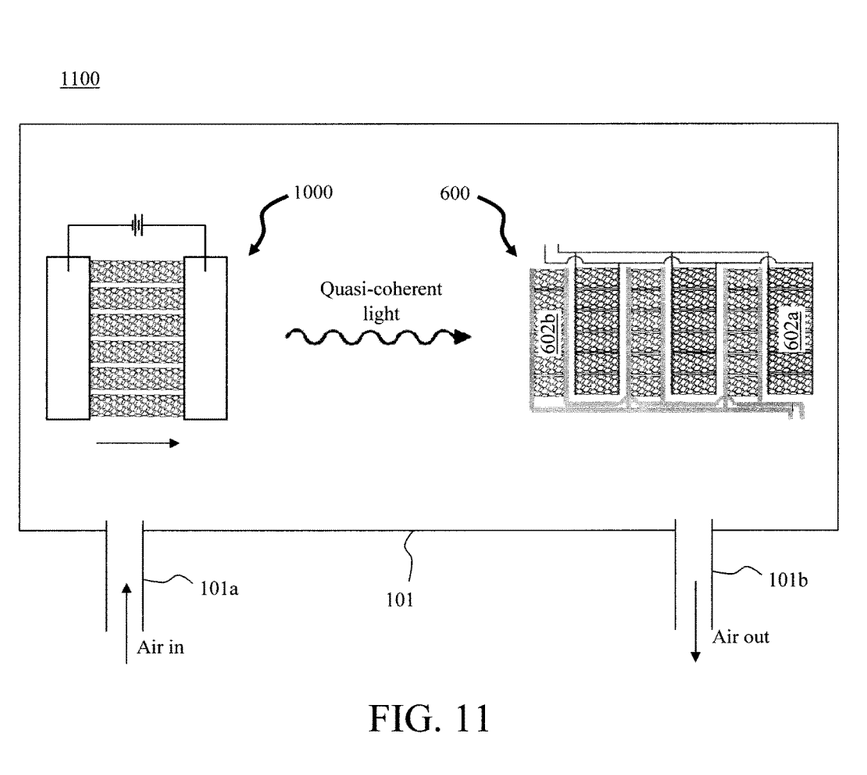
FIG. 11 is a diagram illustrating an exemplary plasmonic, non-dispersive infrared gas sensor employing the carbon nanotube plasmonic resonance detector of FIG. 6 and the plasmonic light source of FIG. 10 according to an embodiment of the present invention.

FIG. 11 is a diagram illustrating an exemplary gas sensor 1100 employing carbon nanotube plasmonic resonance detector 600 (of FIG. 6) and plasmonic light source 1000 (of FIG. 10). In this example, the same general set-up is used as in FIG. 1, i.e., the light source and plasmonic resonance detector being present within an enclosure 101 with the light source being incident on the plasmonic resonance detector. Thus, like structures are numbered alike in the figures.

Figure 12:
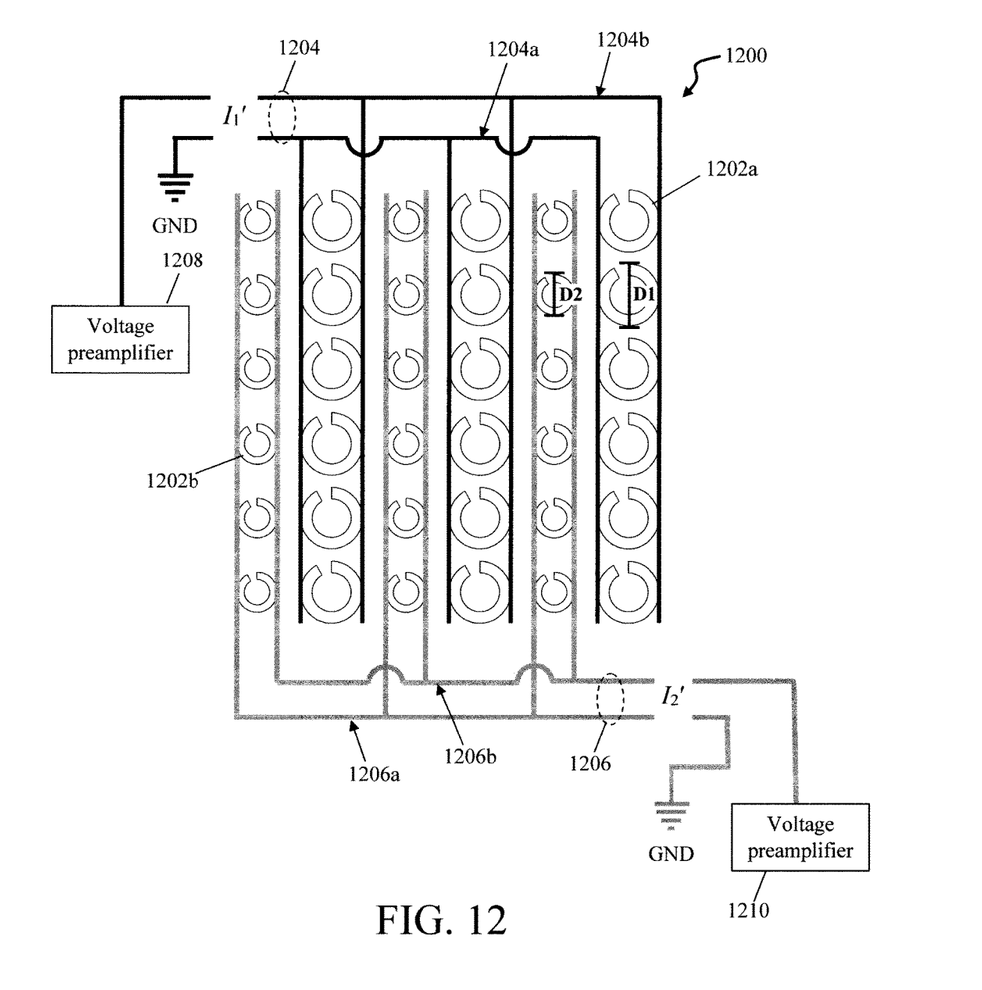
FIG. 12 is a diagram illustrating an exemplary split-ring plasmonic resonance detector according to an embodiment of the present invention.

Non-carbon nanotube-based plasmonic resonance differential detector designs are also contemplated herein. See, for example, plasmonic resonance detector 1200 in FIG. 12. As shown in FIG. 12, plasmonic resonance detector 1200 includes a differential plasmon resonator array, where the resonators, i.e., (first and second sets of) plasmonic resonators 1202a and 1202b are split-ring resonators (instead of carbon nanotubes) of different sizes. Leveraging the same general principles described above, based on their different sizes (e.g., diameters D1 and D2, respectively) the split-ring resonators 1202a and 1202b are configured to be resonant with light at different wavelengths—thereby providing a differential signal. According to an exemplary embodiment, the first set of split-ring resonators is resonant at the absorption peak of a target gas, and the second set of split-ring resonators provides a differential signal at a slightly different wavelength, or vice versa. For instance, by way of example only, the larger resonators (split-ring resonators 1202a of diameter D1) can have a resonance at 4.3 µm, at the $CO_2$ absorption band, and the smaller resonators (split-ring resonators 1202b of diameter D2) can have a resonance at 4.0 µm (a reference wavelength), providing the differential signal.

With the split-ring resonators, the resonant wavelength is approximately proportional to the diameter (i.e., D1, D2, etc.) of the resonator. The width of the split-ring resonator (i.e., outer diameter minus inner diameter) and the out-of-plane height would be chosen so that the resonators effectively confine light, and the diameter would be chosen so that the appropriate wavelength resonator is obtained.

As shown in FIG. 12, (first and second) metal contacts 1204 and 1206 are formed to the split-ring resonators 1202a and 1202b, respectively. Specifically, the metal contacts 1204 are formed contacting the split-ring resonators 1202a (having size S1), and the metal contacts 1206 are formed contacting the split-ring resonators 1202b (having size S2).

The metal contacts 1204 and 1206 are used to extract the target gas absorption signal ($I_1'$) and the reference signal ($I_2'$) from the split-ring resonators 1202a and 1202b, respectively, via photothermoeletric transduction (see above). For instance, in the non-limiting example provided above, the metal contacts 1204 are used to extract the $CO_2$ absorption signal ($I_{4.3}$), and the metal contacts 1206 are used to extract the reference signal ($I_{4.0}$).

According to an exemplary embodiment, one contact to each split-ring resonator is grounded while the other is connected (through wirebonds, chip carriers, etc.—not shown) to a voltage preamplifier, which will convert the photovoltage to a macroscopic voltage that can be outputted. Specifically, as shown in FIG. 12, metal contacts 1204 to split-ring resonators 1202a (i.e., the target gas signal resonators) include a first contact 1204a which is grounded and a second contact 1204b that is connected to a voltage preamplifier 1208. Likewise, metal contacts 1206 to split-ring resonators 1202b (i.e., the reference signal resonators) include a first contact 1206a which is grounded and a second contact 1206b that is connected to a voltage preamplifier 1210.

Figure 13:
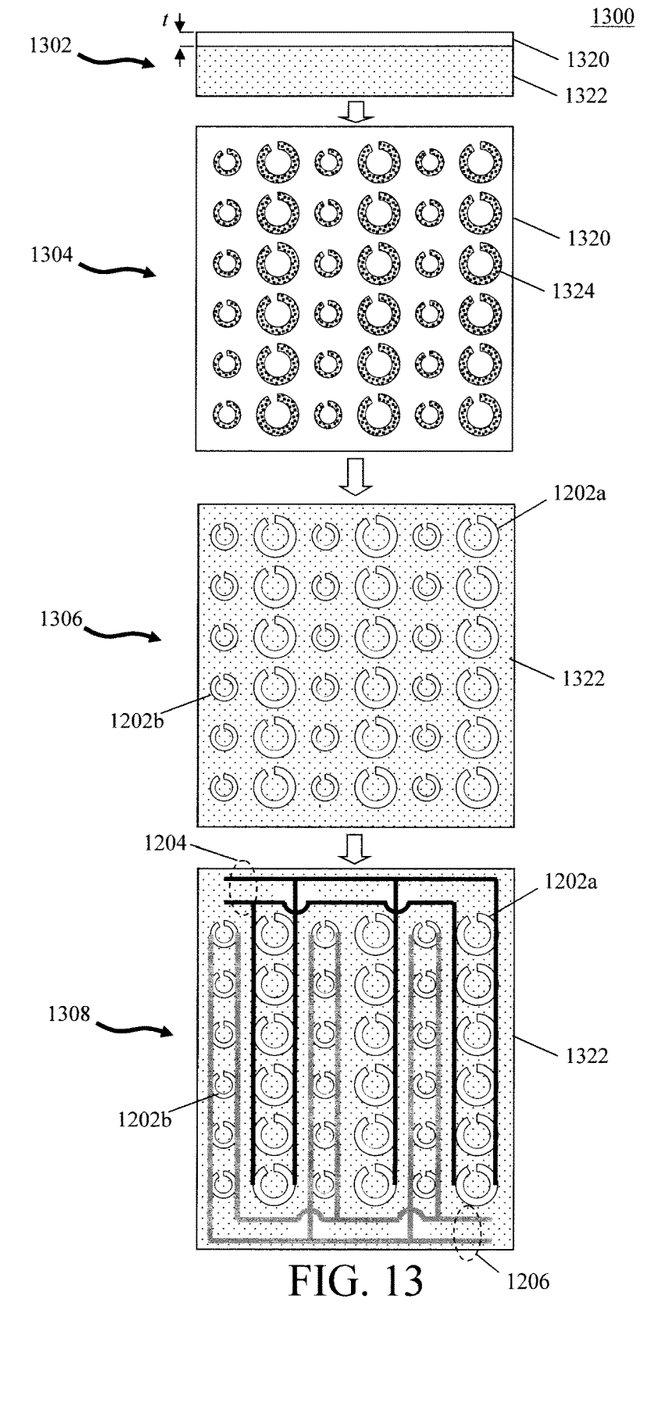
FIG. 13 is a diagram illustrating an exemplary methodology for forming the split-ring plasmonic resonance detector of FIG. 12 according to an embodiment of the present invention.

An exemplary methodology 1300 for forming plasmonic resonance detector 1200 (of FIG. 12) is now described by way of reference to FIG. 13. In step 1302, a thin film 1320 (e.g., having a thickness t of from about 30 nm to about 500 nm and ranges therebetween) of the resonator material is deposited onto an insulating substrate 1322. Step 1302 is depicted via a cross-sectional side view in FIG. 13. Suitable resonator materials include, but are not limited to, gold (Au), titanium nitride (TiN) and/or graphene. According to an exemplary embodiment, the insulating substrate 1322 includes, but is not limited to, high-resistivity Si, plastic, and glass. In another exemplary embodiment, the insulating substrate 1322 includes an insulating layer (on which the detector is formed) over a semiconductor. For instance, by way of example only, the insulating substrate 1322 can include a bulk semiconductor (e.g., Si, Ge, SiGe, III-V, etc.) wafer covered with a dielectric such as $SiO_2$, $HfO_2$ and/or $Al_2O_3$. As provided above, use of a semiconductor under the insulator enables the implementation of electronics in the semiconductor (e.g., detector readout electronics and signal processing) that support the detector.

Switching to a top-down view, in step 1304 a patterned mask 1324 is then formed on the thin film 1320 marking the footprint and location of the split-ring resonators having different sizes/diameters. According to an exemplary embodiment, the mask 1324 defines split-ring resonators having at least two diameters, D1 and D2—see above. By way of example only, as described above, D1 can correspond to the 4.3 µm $CO_2$ absorption and D2 to the 4.0 µM reference. The mask 1324 can include a standard hardmask material such as SiN patterned using standard optical lithography and etching techniques or a PMMA/HSQ mask patterned using e-beam lithography.

In step 1306, an etch is used to transfer the mask 1324 to the thin film 1320, forming the split-ring resonators having at least two diameters. For instance, in the example shown in FIG. 13, the thin film 1320 is patterned into split-ring resonators 1202a and 1202b having two diameters D1 and D2, wherein D1>D2. By way of example only, as provided above, D1 can correspond to the 4.3 µm $CO_2$ absorption and D2 to the 4.0 µm reference. Suitable etching processes include, but are not limited to, RIE in a plasma such as oxygen plasma. Following the resonator etch, any remaining mask 1324 can be removed.

Finally, in step 1308 metal contacts 1204 and 1206 are formed to the split-ring resonators 1202*a* and 1202*b*, respectively. Standard metallization techniques can be employed. Suitable contact metals include, but are not limited to, Cu, Ni, Pt and/or Pd.

Figure 14:
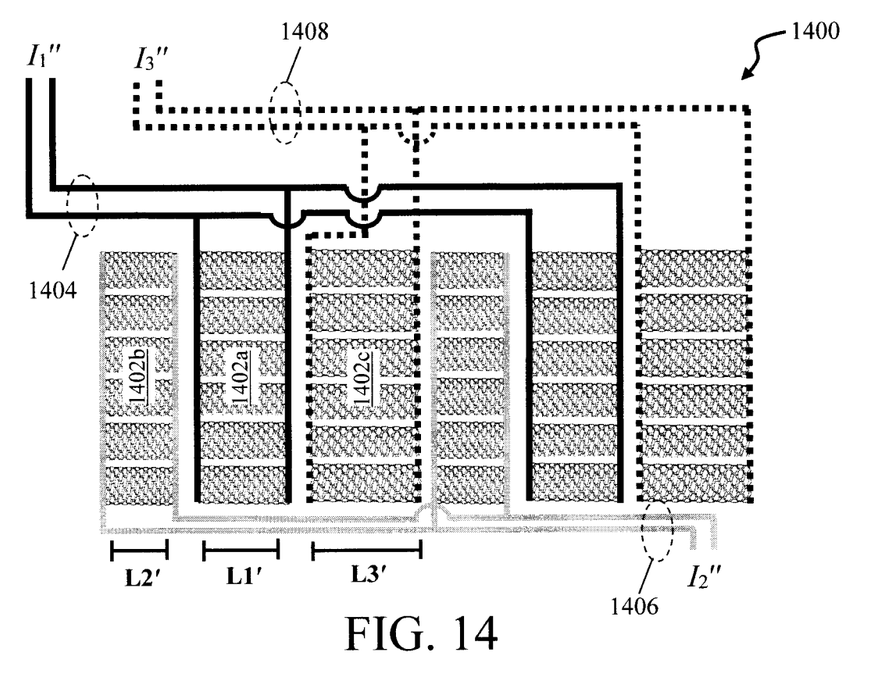
FIG. 14 is a diagram illustrating an exemplary plasmonic resonance detector for the detection of multiple target gases according to an embodiment of the present invention.

In the examples above, reference was made to differential plasmon resonator arrays having resonators corresponding to the peak absorption wavelength of a target gas and a reference wavelength. The same concepts can be leveraged to extend the capabilities of the present gas sensors to detect multiple target gases (i.e., a first target gas, a second target gas, etc.) simply by expanding the array to include additional (interwoven) resonators. By way of example only, the plasmon resonator array 1400 shown in FIG. 14 includes ribbons 1402*a*, 1402*b* and 1402*c* of carbon nanotubes having three different lengths, e.g., lengths L1', L2' and L3'—respectively, whereby the ribbons 1402*a* of carbon nanotubes having the first length L1' are resonant at a first wavelength, the ribbons 1402*b* of carbon nanotubes having the second length L2' are resonant at a second wavelength, and the ribbons 1402*c* of carbon nanotubes having the third length L3' are resonant at a third wavelength. By way of example only, the lengths L1', L2' and L3' might correspond to the absorption peaks of a first target gas, a reference wavelength and a second target gas, generating photocurrent signals $I_1''$, $I_2''$ and $I_3''$, respectively.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A gas sensor, comprising:
   a plasmonic resonance detector comprising a differential plasmon resonator array that is resonant at different wavelengths of light; and
   a light source incident on the plasmonic resonance detector, wherein the light source comprises:
   a first electrode;
   a second electrode;
   a plurality of plasmonic resonators between the first electrode and the second electrode; and
   a voltage source configured to apply a voltage across the first electrode and the second electrode causing current to pass through the plasmonic resonators.

2. The gas sensor of claim 1, further comprising:
   an enclosure, wherein the plasmonic resonance detector and the light source are housed within the enclosure.

3. The gas sensor of claim 1, wherein the enclosure comprises:
   an air inlet; and
   an air outlet.

4. The gas sensor of claim 1, wherein the plurality of plasmonic resonators comprise aligned carbon nanotubes.

5. The gas sensor of claim 1, wherein the differential plasmon resonator array comprises:
   at least one first set of plasmonic resonators interwoven with at least one second set of plasmonic resonators, wherein the at least one first set of plasmonic resonators is configured to be resonant with light at a first wavelength, and wherein the at least one second set of plasmonic resonators is configured to be resonant with light at a second wavelength.

6. The gas sensor of claim 5, wherein the differential plasmon resonator array further comprises:
   at least one third set of resonators interwoven with the at least one first set of plasmonic resonators and the at least one second set of plasmonic resonators, wherein the at least one third set of plasmonic resonators is configured to be resonant with light at a third wavelength.

7. The gas sensor of claim 6, wherein the first wavelength corresponds to a peak absorption wavelength of a first target gas, and wherein the second wavelength corresponds to a reference wavelength.

8. The gas sensor of claim 7, wherein the third wavelength corresponds to a peak absorption wavelength of a second target gas.

9. The gas sensor of claim 5, wherein the differential plasmon resonator array comprises:
   a first set of ribbons of carbon nanotubes having a length L1 interwoven with a second set of ribbons of carbon nanotubes having a length L2, wherein the carbon nanotubes of the length L1 are configured to be resonant with light at the first wavelength, and wherein the carbon nanotubes of the length L2 are configured to be resonant with light at the second wavelength.

10. The gas sensor of claim 9, further comprising:
    first metal contacts to the first set of ribbons of carbon nanotubes having the length L1; and
    second metal contacts to the second set of ribbons of carbon nanotubes having the length L2.

11. The gas sensor of claim 5, wherein the differential plasmon resonator array comprises:
    a first set of split-ring resonators having a diameter D1 interwoven with a second set of split-ring resonators having a diameter D2, wherein the split-ring resonators having the diameter D1 are configured to be resonant with light at the first wavelength, and wherein the split-ring resonators having the diameter D2 are configured to be resonant with light at the second wavelength.

12. The gas sensor of claim 11, wherein the first set of split-ring resonators and the second set of split-ring resonators are each formed from a material selected from the group consisting of: gold (Au), titanium nitride (TiN), graphene, and combinations thereof.

13. A method for analyzing a target gas, comprising the steps of:
    illuminating the target gas with light from a light source, wherein the light is incident on a plasmonic resonance detector comprising a differential plasmon resonator array having at least one first set of plasmonic resonators interwoven with at least one second set of plasmonic resonators, wherein the at least one first set of plasmonic resonators is configured to be resonant with the light at a first wavelength corresponding to a peak absorption wavelength of the target gas, wherein the at least one second set of plasmonic resonators is configured to be resonant with the light at a second wavelength corresponding to a reference wavelength, wherein the differential plasmon resonator array comprises a first set of ribbons of carbon nanotubes having a length L1 interwoven with a second set of ribbons of carbon nanotubes having a length L2, wherein the carbon nanotubes of the length L1 are configured to be resonant with the light at the first wavelength, and wherein the carbon nanotubes of the length L2 are configured to be resonant with the light at the second wavelength;
    absorbing the light by the at least one first set of plasmonic resonators and the at least one second set of plasmonic resonators, wherein the light at the first wavelength incident on the at least one first set of plasmonic resonators is dependent on an amount of the light at the first wavelength absorbed by the target gas;

generating a photocurrent signal $I_1$ in the at least one first set of plasmonic resonators and a photocurrent signal $I_2$ in the at least one second set of plasmonic resonators; and determining a concentration of the target gas using $I_1$-$I_2$.

14. A method for forming a plasmonic resonance detector, comprising the step of:

forming at least one first set of plasmonic resonators interwoven with at least one second set of plasmonic resonators, wherein the at least one first set of plasmonic resonators is configured to be resonant with light at a first wavelength corresponding to a peak absorption wavelength of a target gas, and wherein the at least one second set of plasmonic resonators is configured to be resonant with light at a second wavelength corresponding to a reference wavelength, wherein the method further comprises the steps of:

forming a film of aligned carbon nanotubes on a substrate;

patterning the film of aligned carbon nanotubes into a first set of ribbons of carbon nanotubes having a length L1 interwoven with a second set of ribbons of carbon nanotubes having a length L2, wherein the carbon nanotubes of the length L1 are configured to be resonant with light at the first wavelength, and wherein the carbon nanotubes of the length L2 are configured to be resonant with light at the second wavelength; and forming contacts to the first set of ribbons of carbon nanotubes and the second set of ribbons of carbon nanotubes.

* * * * *